US008039257B2

(12) United States Patent
Beschorner

(10) Patent No.: US 8,039,257 B2
(45) Date of Patent: Oct. 18, 2011

(54) PRE-TRANSPLANT ACCOMODATED ORGANS RESISTANT TO ANTI-DONOR IMMUNITY

(75) Inventor: William E Beschorner, Omaha, NE (US)

(73) Assignee: The Board of Regents of the University of Nebraska, Omaha, NE (US)

( * ) Notice: Subject to any disclaimer, the term of this patent is extended or adjusted under 35 U.S.C. 154(b) by 0 days.

(21) Appl. No.: 12/897,297

(22) Filed: Oct. 4, 2010

(65) Prior Publication Data

US 2011/0020295 A1 Jan. 27, 2011

Related U.S. Application Data

(62) Division of application No. 10/181,896, filed as application No. PCT/US01/02342 on Jan. 25, 2001, now Pat. No. 7,807,463.

(60) Provisional application No. 60/178,347, filed on Jan. 25, 2000.

(51) Int. Cl.
A61K 35/32 (2006.01)
(52) U.S. Cl. ......................................... 435/377; 424/549
(58) Field of Classification Search .................. None
See application file for complete search history.

(56) References Cited

U.S. PATENT DOCUMENTS 6,060,049 A    5/2000  Beschorner

FOREIGN PATENT DOCUMENTS

WO    9427622 A1    12/1994
WO    9847529       10/1998
WO    0154722 A1    8/2001

OTHER PUBLICATIONS

Beschorner et al., "Induction of human chimerism and functional suppressor cells in fetal pigs: feasibility of surrogate tolerogenesis for xenotransplantation," Transplant Proc. Apr. 1996;28(2):648-9.
Fontes et al., "Evidence for engraftment of human bone marrow cells in non-lethally irradiated baboons," Transplantation. Dec. 15, 1997;64(11):1595-8.
Fu et al., "Prevention and restoration of second-set liver allograft rejection in presensitized mice: the role of "passenger "leukocytes, donor major histocompatibility complex antigens, and host cytotoxic effector mechanisms," Transplantation. Feb. 15, 1999;67(3):444-50.
He et al., "Impact of different forms of recipient antigen and different routes of antigen administration in donor pretreatment for preventing graft-versus-host disease in rat small bowel transplantation," Transplant Proc. Oct. 1996;28 (5):2469.
Lin Y et al., "Accommodation and T-Independent B Cell Tolerance in Rats With Long Term Surviving Hamster Heart Xenografts," J. Immunol., Jan. 1998; 160: 369-375.
Lin Y et al., "Accommodated xenografts survive in the presence of anti-donor antibodies and complement that precipitate rejection of naive xenografts," J Immunol. Sep. 1, 1999;163(5):2850-7.

Lin Y et al., "Long-term survival of hamster hearts in presensitized rats," J Immunol. May 1, 2000;164(9):4883-92.
Angelini et al., "Antibody-mediated rejection without acute graft dysfunction in adult ABO-compatible heart transplantation: a case of accommodation," J. Heart Lung Transplant. Dec. 2008;27(12):1357-60.
Yang et al "Chimeric pig hearts resist hyperacute rejection in ex vivo perfusion model," J. Extra Corpor Technol. Sep. 2001;33(3):181-4.
Lin et al., "Blockade of induced xenoantigen expression prevents rejection after retransplantation of accommodated hamster-to-rat heart xenografts," Transplantation. Feb. 15, 1998;65(3):340-5.
Higgins et al., "Blood levels of donor-specific human leukocyte antigen antibodies after renal transplantation: resolution of rejection in the presence of circulating donor-specific antibody," Transplantation. Oct. 15, 2007;84(7):876-84.
Shishido et al., "ABO-incompatible living-donor kidney transplantation in children," Transplantation. Sep. 27, 2001;72 (6):1037-42.
Wu et al., "A novel immunocompetent rat model of HCV infection and hepatitis," Gastroenterology. May 2005;128 (5):1416-23.
Wu et al., "Hepatitis B virus infection of transplanted human hepatocytes causes a biochemical and histological hepatitis in immunocopetentent rats," World J Gastroenterol. May 2003;9(5):978-83.
Ouyang et al., "Transplantation of human hepatocytes into tolerized genetically immunocompetent rats," World J Gastroenterol. Jun. 2001;7(3):324-30.
Wu et al., "Human hepatocytes transplanted into genetically immunocompetent rats are susceptible to infection by hepatitis B virus in situ," J Viral Hepat. Mar. 2001;8(2):111-9.
Colvin, "Antibody-mediated renal allograft rejection: diagnosis and pathogenesis," J Am Soc Nephrol. Apr. 2007;18 (4):1046-56. Epub Mar. 14, 2007.
Beschorner et al., "Pre-transplant analysis of accommodation in donor pigs," Xenotransplantation 10, 66-71, 2003.
Dorling et al., "In vitro accommodation of porcine endothelial cells by low dose human anti-pig antibody: reduced binding of human lymphocytes by accommodated cells associated with increased nitric oxide production," Xenotransplantation 5:84-92, 1998.
Mohiuddin, M et al., "Antibody-mediated accommodation of heart grafts expressing an incompatible carbohydrate antigen." Transplantation, Feb. 15, 2003, vol. 75, No. 3. pp. 258-262.
Fontes et al., "Evidence for Engraftment of Human Bone Marrow Cells in Non-Lethally Irradiated Baboons," Dec. 15, 1997, vol. 64, No. 11, pp. 1595-1630.
Parker et al., Immunol Today. Aug. 1996; 17(8): 373-8.
Dalmasso et al., Molecular Immunology, (Apr.-May 1998) vol. 35, No. 6-7, p. 341.

(Continued)

Primary Examiner — Zachary Skelding
(74) Attorney, Agent, or Firm — Banner & Witcoff, Ltd.

(57) ABSTRACT

This invention includes the composition of organ grafts accommodated prior to transplantation and therefore resistant to rejection by preformed antibodies. Accommodation is achieved within the donor animal by administration of sublethal levels of accommodation inducing factors derived from animals sensitized to the donor.

5 Claims, 3 Drawing Sheets

OTHER PUBLICATIONS

Figure 1:
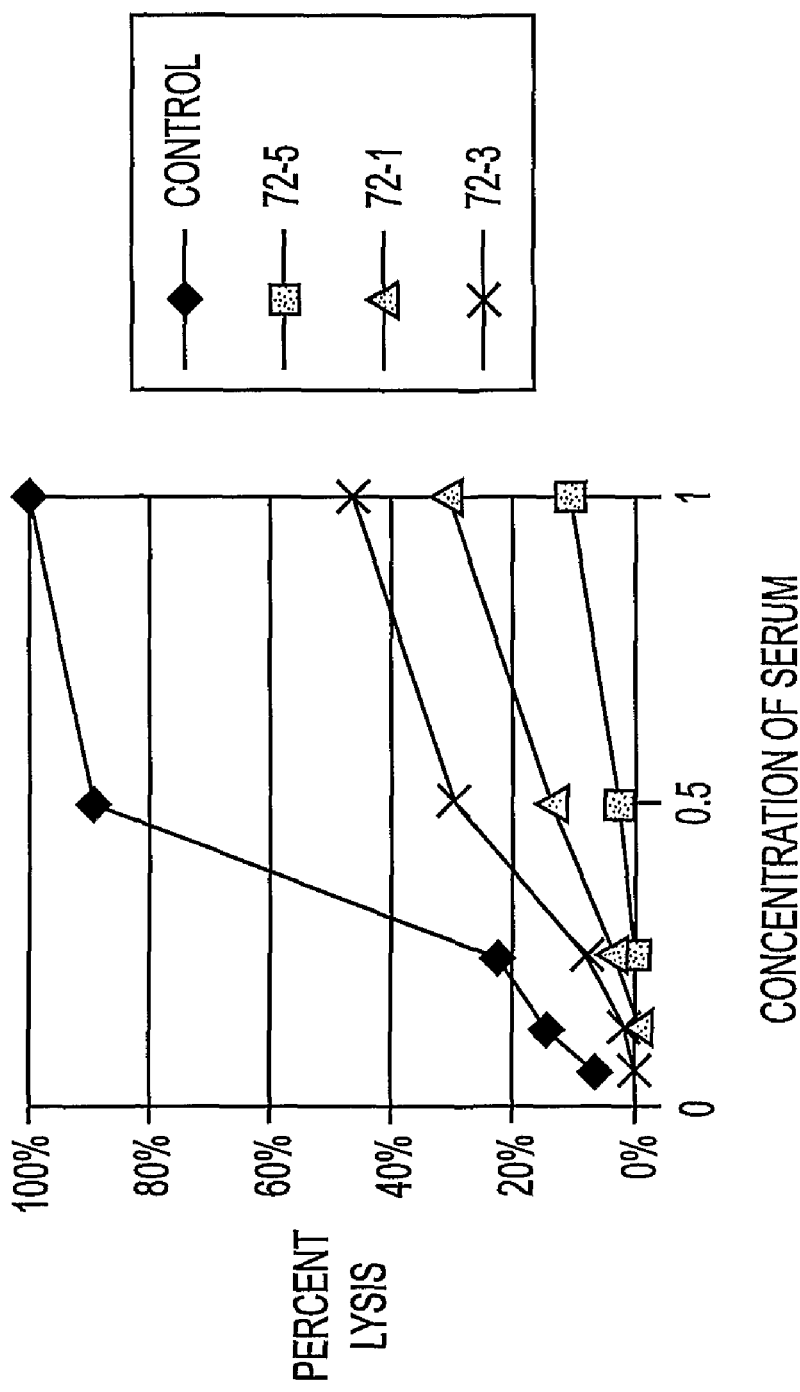

Dalmasso et al., Xenotransplantation, 3:54-62 (1996).
Palmeshofer et al., Transplantation. Apr. 15, 1998; 65(7): 971-8.
Parker et al., J. Immunol. Oct. 15, 1994;153(8):3791-803.
Stanley et al., Proc Natl. Acad. Sci. USA. Jan. 1979; 76(1): 303-7.
Galili et al., "The human natural anti-Gal IgG. III. The subtlety of immune tolerance in man as demonstrated by crossreactivity between natural anti-Gal and anti-B antibodies," J Exp Med. Mar. 1, 1987;165(3):693-704.
Friedman et al., "Human CD4+ T cells mediate rejection of porcine xenografts," J Immunol. May 1, 1999;162 (9):5256-62.
Sudan et al., "Effect of Surrogate Tolerogenesis on the Vascular ejection of Pig Heart Xenografts", Transplantation, Jan. 27, 2000, pp. 232-235, vol. 69, No. 2, Lippincott Williams & Wilkins, Inc.
Kim et al., "Microchimerism and Tolerance after in Utero Bone Marrow Transplantation in Mice", Journal of Surgical Researach, 1998, pp. 1-5, vol. 77, Article No. JR975255, Academic Press.
Sablinski et al., "Long-Term Discordant Xenogenic (Porcine-to-Primate) Bone Marrow Engraftment in a Monkey treated with Porcine-Specific Growth Factors", Transplantation, Apr. 1999, pp. 972-977, vol. 67, No. 7, Lippincoll Williams & Wilkins, Inc.

PRE-TRANSPLANT ACCOMODATED ORGANS RESISTANT TO ANTI-DONOR IMMUNITY

CROSS-REFERENCE TO RELATED APPLICATIONS

This application is a divisional of Ser. No. 10/181,896 filed Nov. 7, 2002, now U.S. Pat. No. 7,807,463, which is a national phase of PCT/US01/02342, filed Jan. 25, 2001, which claims priority to U.S. Provisional Application No. 60/178,347, now expired, filed Jan. 25, 2000. Each of these applications is incorporated herein by reference in its entirety.

This invention was made with government support under Research Grant No. R43 DK50737 awarded by the U.S. government. The government has certain rights in the invention.

BACKGROUND OF THE INVENTION

I. Field of the Invention

The field of the present invention relates to the transplantation of organs and tissues, and particularly to the conditioning of a xenograft organ while still in the donor to resist rejection antibodies in the graft recipient (accommodation). The invention also relates to methods for assessing accommodation within the donor animal.

II. Background

A major barrier to the transplantation of organs from one mammalian species to another is rejection of the xenografts. Much of the rejection is not related to tissue-specific antigens but results from the recipient being sensitized to the donor animal. For example, humans and Old World monkeys have circulating antibodies to the alpha galactosyl oligosaccharide expressed on tissues in other animals, including pigs. The antibodies bind to any transplanted pig xenograft, bind complement, and destroy the graft within an hour. This rapid reaction is referred to as hyper-acute rejection (HAR). The graft is rapidly destroyed by the binding of preformed natural antibodies to endothelial cells and fixation of the complement. Most of the preformed antibodies in humans and old world apes (>80%) are against Gal(alpha)1-3Gal epitopes (alphaGal).

Acute vascular xenograft rejection occurs at three to eight days post transplant. Induced and recurrent anti-donor antibodies bind to the endothelium, leading to endothelial activation, small vessel thrombosis, and recruitment of macrophages and NK cells. Acute xenograft rejection is also mediated by cellular rejection. In contrast to cellular allograft rejection, CD4+ cytotoxic lymphocytes contribute to the graft injury.

The current methods for prevention of HAR target the binding of antibody or the fixation of complement. Anti-donor antibodies or complement can be depleted from the blood of the recipient. Hyper-acute rejection was prevented in ABO mismatched cardiac allografts performed in baboons by infusion of soluble trisaccharides of the A and B antigen to neutralize the antibodies. Though the circulating antibodies persisted after discontinuing the oligosaccharides, some grafts showed prolonged survival. Cooper D. K., et al., *Transplantation* 56: 769-77 (1993). Transgenic pigs which express human complement inhibitors or with reduced expression of alphaGal have been created.

These technologies are useful on a short-term basis; however, they are not completely effective. Antibodies return rapidly after their removal and the procedure must be repeated frequently. Transgenic pigs are variable in the level of expression of the transgene. With both methodologies, episodes of HAR and acute vascular rejection are common. Efforts to suppress acute xenograft rejection using conventional chemotherapy have been only partially successful. In particular, the antibody response to pig xenografts has proved resistant to suppression.

To reliably achieve long-term survival of xenografts, immune tolerance or graft accommodation will be necessary. Immune tolerance involves programming the recipient's immune system to be specifically unresponsive to the graft. Accommodation refers to adaptation of the graft to be resistant to an existing immune response.

Partial immune tolerance to pig xenografts has been induced by ablating the recipient immune system and reconstituting it in the presence of porcine hematopoietic cells. Porcine hematopoietic cells are detectable a year later. This approach has three basic limitations. First, tolerance would not resolve the problem caused by pre-existing natural antibodies. Additional efforts, such as removal of pre-existing antibodies by immune adsorption would be required. Second, the recipient is subject to a prolonged period of immune deficiency, putting it at risk for opportunistic and zoonotic infections. Third, the tolerance would be to antigens expressed on the hematopoietic cells only. Tolerance would not be induced to the tissue-associated antigens. Pig heart and kidney xenografts were fulminantly rejected in baboons using this protocol.

The transplantation of pig thymi into immune ablated recipients enhances tolerance as the recipient pre-thymocytes mature in the porcine environment. Using this approach, porcine skin graft survival is markedly prolonged in mice and modestly prolonged in primates. The basic limitations described above with mixed chimerism would still be a problem.

Patent application No. PCT/US94/05844 teaches the induction of immune tolerance of recipient lymphocytes to xenografts by infusing lymphocytes into immune deficient donor animals. The tolerant cells are later harvested and transferred back to the recipient, conveying tolerance to the recipient. However, the preexisting immune response would limit the usefulness of that approach.

The mechanism of accommodation is unknown. It is not due to the depletion of antibodies or to replacement of donor endothelium with host endothelium within the graft. Immunohistochemistry of long term cardiac xenografts (hamster-to-rat) shows deposition of IgG, IgM, C3, and C6 on the endothelium, but minimal fibrin formation.

The possibility has been explored that accommodated endothelial cells have reduced expression of antigen. Though some reduction in antigens such as alpha gal was observed with accommodation, it was not thought to be sufficient to protect the graft. Parker W. et al., *Am. J. Pathol.* 152: 829-39 (1998).

It is known that accommodated grafts can be adoptively transplanted to a second recipient. The factors responsible for accommodation are present within the graft and do not require circulating regulatory cells or factors. Miyatake showed that if rejection of a hamster heart graft can be prevented in a rat recipient, the graft will also resist rejection when re-transplanted into a second recipient identical with the first recipient. T. Miyatake, N. Koyamada, W. W. Hancock, M. P. Soares, and F. H. Bach. Survival of accommodated cardiac xenografts upon re-transplantation into cyclosporine-treated recipients. Transplantation 65: 1563-1569, (1998). While the observation is of scientific value, it is not clinically useful. To apply this observation would require two identical subjects, such as human recipients, one who would host the donor organ until accommodation is achieved. The organ would then be procured and transplanted into the second subject. The very limited number of potential recipients with identical twins and the ethically unacceptable complications to the first recipient make this approach unfeasible.

Some success in achieving accommodation in cultured endothelial cells has been reported. Dorling A., et al., *Xenotransplantation,* 5: 84-92 (1998); and Dorling A., et al., *Transplantation,* 62: 1127-1136 (1996). Dorling et al. demonstrated that prolonged exposure in culture of porcine endothelial cells to normal human immunoglobulins produced endothelial cell changes suggestive of accommodation.

Apparent confirmation of these studies was provided by Shah et al., *Fifth Congress of the International Xenotransplantation Association,* Abstract 199 (1999). Minimal resistance to complement mediated cytotoxicity was achieved with 72 hours of culture. Better resistance was observed with 120 to 144 hours of incubation. On the other hand, others. were unable to confirm these studies using primary endothelial cell cultures. McKane W. et al. *Fifth Congress of the International Xenotransplantation Association,* Abstract 200 (1999). They suggested that the apparent resistance reported by others may be an artifact related to the use of immortalized endothelial cells, which constitutively express anti-apoptotic genes.

In vitro culture is unlikely to have significant clinical utility. Accommodated endothelial cells would not have significant utility by themselves. Furthermore, accommodation of cultured and transformed endothelial cells required a minimum of 72 hours and preferably 120 hours of culture. See Dorling et al. (1996), supra. If the observation were to be extended to ex vivo culture of whole organs maintained in culture, the organs would significantly deteriorate during this period.

Achieving accommodation within the recipient is very difficult, costly, and often ends in failure, with rejection of the graft.

Therefore, a need exists for a method of xenograft transplantation that avoids the high costs, the complications, and the high risk of failure associated with accommodation of the xenograft organ within the recipient after transplantation.

III. SUMMARY OF THE INVENTION

An objective of the invention is to provide a tissue or a graft accommodated prior to transplantation of the tissue or graft.

A second objective of the invention is to provide a method for accommodation of the donor graft prior to transplantation.

Another objective of the invention is to provide a method for development of improved in-donor accommodation technology.

In accordance with one embodiment of the invention, a method to produce a tissue or organ accommodated in a donor mammal to resist rejection in a recipient mammal, is provided. The method comprises:

infusing a donor mammal at least one time with sub-lethal levels of at least one accommodation-inducing factor; allowing prolonged exposure to said accommodation inducing factor; and harvesting one or more of the tissues or organs which are accommodated.

In accordance with a preferred embodiment, the accommodation-inducing factor is infused in a donor mammal which is in an immune deficient state. In accordance with another preferred embodiment, the accommodation-inducing factor is an antibody reactive with donor endothelium, such as pig endothelium, plasma cells, B lymphocytes, human B lymphocytes, conditionally immortalized B lymphocytes, anti-alphaGal antibody, a cell expressing an accommodation inducing factor such as an antibody, a hybridoma comprising a cell expressing an accommodation inducing factor, T cells reactive with cells in the graft tissue or organ, perforin, or *Bandeiraea simplicifolia* lectin. In accordance with another preferred embodiment, the method further comprises the step of determining that accommodation of the tissue or organ has been achieved, prior to transplantation of said organ or tissue.

In accordance with another embodiment, a xenograft organ or tissue is provided. The xenograft organ or tissue is raised in a donor mammal treated with an accommodation inducing factor. In accordance with a preferred embodiment, the xenograft organ includes, but is not limited to a heart, a kidney, a liver, a lung, a pancreas, a heart-lung intestine, a spleen, or a thymus. The xenograft tissue includes but is not limited to bone, skin, hair, eye, neural tissue, smooth muscle, skeletal muscle, cardiac muscle, myocytes, pancreatic islets, hepatocytes, embryonic stem cells, progenitor cells, or hematopoietic cells. In accordance with another preferred embodiment, the treatment with an accommodation inducing factor occurred while the donor mammal was in an immune deficient state. In accordance with another preferred embodiment, the accommodation inducing factor is an antibody reactive with donor endothelium, an antibody reactive with pig endothelium, plasma cells, B lymphocytes, human B lymphocytes, conditionally immortalized B lymphocytes, anti-alphaGal antibody, a cell expressing an accommodation inducing factor, a hybridoma comprising a cell expressing an accommodation inducing factor, T cells reactive with cells in the graft tissue or organ, perforin, or *Bandeiraea simplicifolia* lectin.

In accordance with yet another embodiment, a method for developing accommodation factors is provided which comprises infusing a donor mammal at least one time with sub-lethal levels of at least one accommodation-inducing factor; administering a tissue or cells from a mammal other than the donor to the donor; allowing prolonged exposure to the accommodation-inducing factor; and harvesting the accommodated tissue or cells. In accordance with a preferred embodiment, the accommodation-inducing factor is from an individual who is the intended recipient of said harvested tissue or cell. In accordance with another preferred embodiment, the accommodation-inducing factor is infused in the donor mammal which is in an immune deficient state. In accordance with yet another preferred embodiment, the accommodation-inducing factor is an antibody reactive with donor endothelium, an antibody reactive with a cell or tissue from a mammal other than said donor which was administered to said donor, a cell expressing an antibody reactive with a cell or tissue from a mammal other than the donor which was administered to said donor, an antibody reactive with pig endothelium, plasma cells, B lymphocytes, human B lymphocytes, conditionally immortalized B lymphocytes, anti-alphaGal antibody, a cell expressing an accommodation inducing factor, a hybridoma comprising a cell expressing an accommodation inducing factor, T cell reactive to the tissue or organ, perforin, or *Bandeiraea simplicifolia* lectin. In accordance with still another preferred embodiment, the method comprises the additional step of determining that accommodation of said tissue or organ has been achieved, prior to harvesting of the tissue or cell.

In accordance with another embodiment, the xenograft tissue or cell is an osteoblast cell, an osteo clost cell, skin, a skin epithelial cell, a hair follicle cell, eye cell, neural cells, a skeletal muscle cell, a smooth muscle cell, a cardiac muscle cell, pancreatic islet, a hematocyte, a stem cell, a progenitor cell, or a hemapoietic cell.

IV. BRIEF DESCRIPTION OF THE DRAWINGS

FIG. 1 shows accommodation in chimeric pigs by a lymphocyte lysis assay. 72-5, 72-1, and 72-3 are chimeric pigs infused at pre-immune fetal stage with bone marrow. The control sample is lymphocytes from an un-infused pig. The lysis was evaluated by Trypan Blue—see Example 3 for detailed method—as a function of the concentration of sensitized sheep serum.

Figure 2:
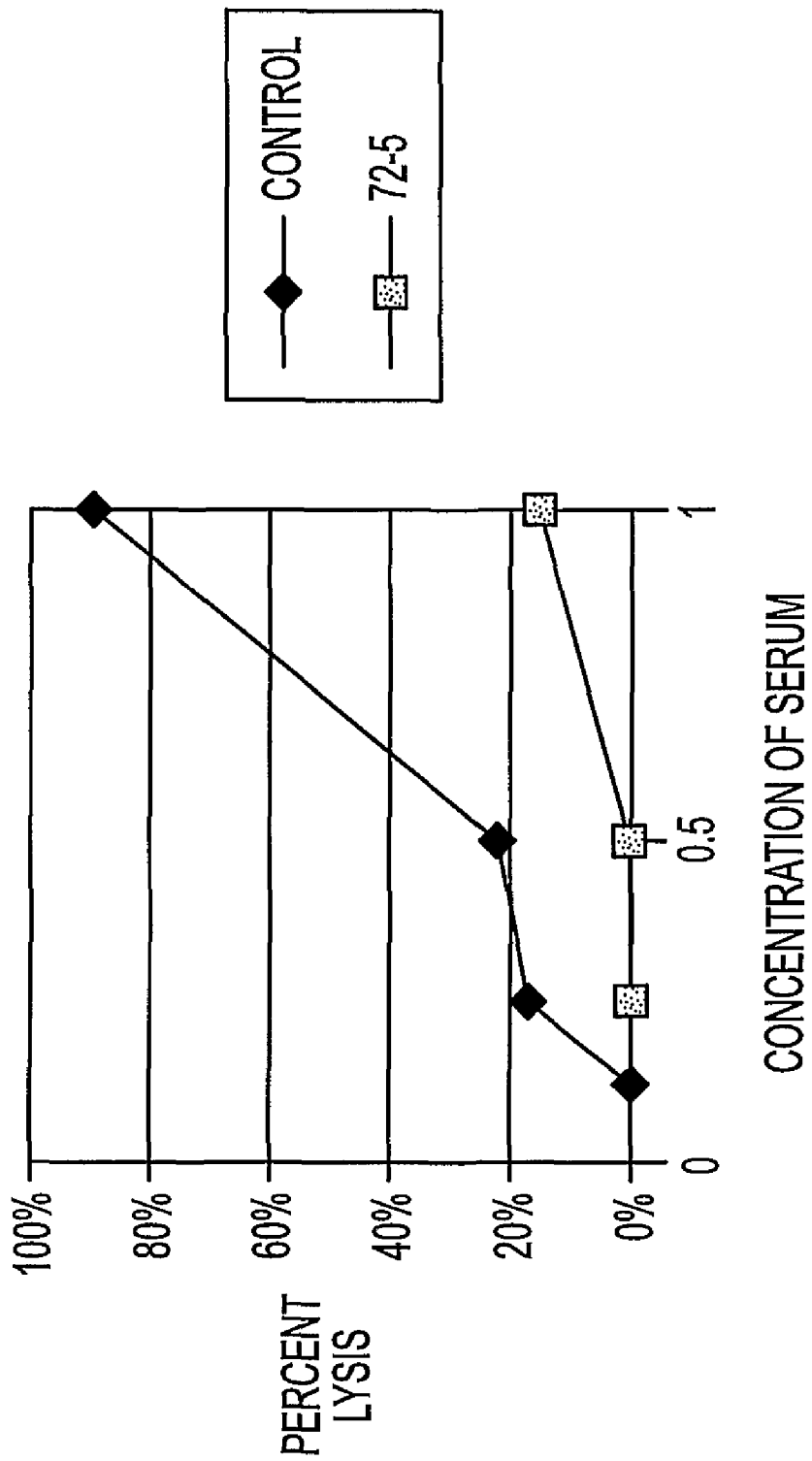

FIG. 2 shows accommodation of a chimeric pig (72-5) by a lymphocyte assay. The control is lymphocytes from an un-infused pig. The lysis was evaluated by Trypan Blue—see Example 3 for detailed method—as a function of the concentration of sensitized sheep serum. The sensitized sheep serum was isolated from a different sensitized sheep than the sheep in FIG. 1.

Figure 3:
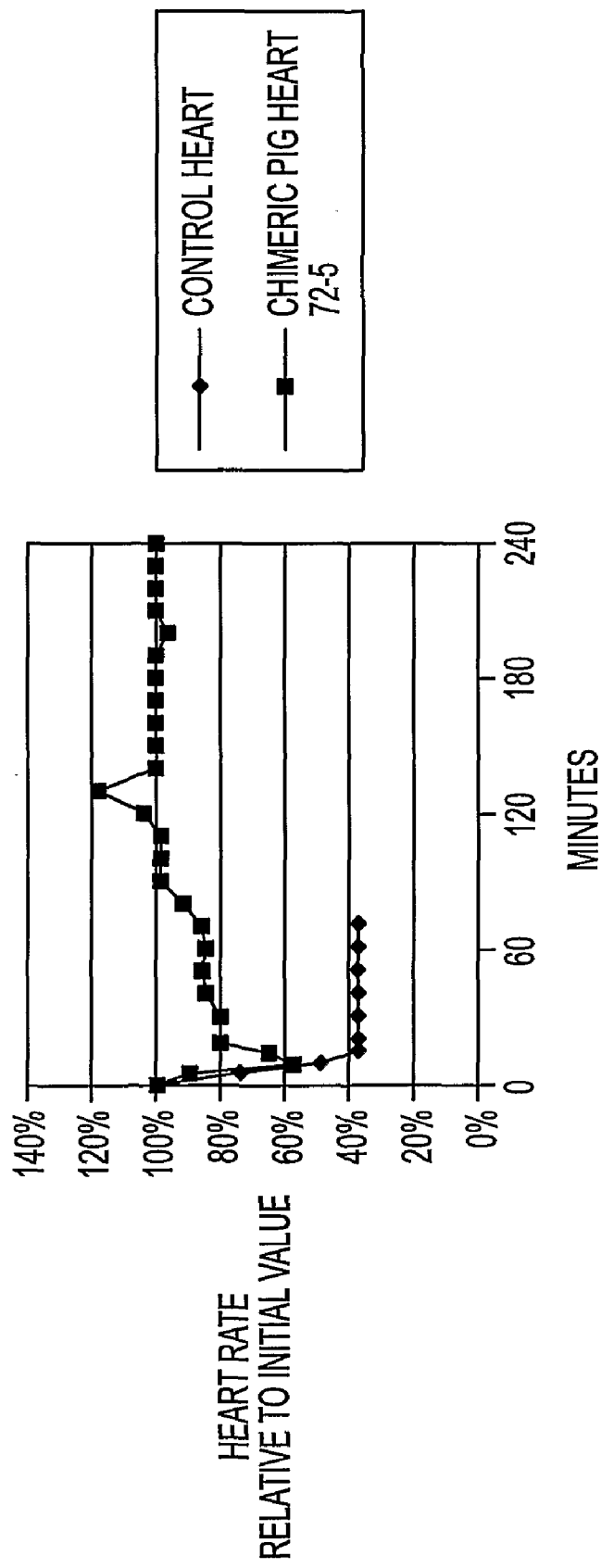

FIG. 3 shows protection of a chimeric pig heart from hyperacute rejection by human blood. The hearts of a control pig and chimeric pig (72-5) were perfused with sensitized human blood and the heart beat was monitored.

V. DETAILED DESCRIPTION OF THE PREFERRED EMBODIMENT

I. Overview

The invention provides a method for production of an accommodated organ or tissue suitable for transplantation and the accommodated organ. Accommodation is the process of conditioning an organ to resist injury in a sensitized recipient. It is also referred to as adaptation. The adaptation conveys resistance in the graft to cell death or apoptosis, procoagulation changes, and adhesion of leukocytes. In accordance with the invention, the accommodation is achieved by infusion of accommodation inducing factor into a donor, allowing the graft to be exposed to the accommodation inducing factor, and harvesting the graft, accommodated while in the donor for resistance to rejection in recipient.

An accommodation-inducing factor is any factor that causes accommodation within a donor of an xenograft organ or tissue. The factor can be an aliquot of plasma from a mammalian species other than the donor. Alternatively, the factor can be a ligand purified from plasma or expressed in an in vitro system. Preferably, the factor is an immune system component, for example a B lymphocyte or an antibody.

The accommodated organ or tissue is an organ or tissue which can resist rejection by a sensitized recipient. A sensitized recipient is any organism with preformed antibodies or memory T cells reactive with donor antigens, present in the graft-recipient prior to transplantation. Examples of sensitized organisms are humans and old world monkeys, sensitive to pig antigens. The sensitized recipient typically produces a hyper-acute and/or acute vascular xenograft immune response to donor tissue, generally. The response is mediated by performed antibodies and T cells present in the recipient organism prior to the introduction of the xenograft. The organ or tissue graft is harvested from a chimeric animal.

In accordance with the invention, a chimeric mammal or animal is any mammal wherein an infused transgenic accommodation-inducing factor resides. For example, a piglet who receives a infusion of cells from another mammal is a chimeric animal. In a preferred embodiment, a chimeric animal is a swine who received, during an immune deficient stage, an infusion of cells from another mammalian species, e.g., a human. The infusion occurs preferably when the donor is in an immune deficient state such as a pre-immune fetus.

Factors that induce accommodation include but are not limited to antibody reactive with donor tissue, antibody reactive with donor endothelium, antibody reactive with pig tissue or endothelium in the case where the donor is a pig or a member of the swine family, plasma cells, B lymphocytes, human B lymphocytes, conditionally immortalized B lymphocytes, anti-alphaGal antibody, a cell engineered to express an accommodation inducing factor, a hybridoma comprising a cell expressing an accommodation inducing factor, and *Bandeiraea simplicifolia* lectin. The factor can be a natural, isolated factor, or it can be a cell engineered to express a ligand or the purified engineered ligand.

The accommodation factors may be derived from a member of a species that would be a xenograft recipient, e.g., a human or another mammal. In a preferred embodiment, the accommodation inducing factors are isolated from an individual who will later become a recipient. The method of determining, isolating, and manipulating each of the accommodations inducing factors are well known to an artisan skilled in the art.

The invention also provides organ xenografts that are less susceptible to rejection by preformed and developing immune elements, particularly antibodies such as natural antibodies to alphaGal. These antibodies are present in most humans and Old World monkeys. The alphaGal antigen is expressed on endothelial cells and other cells or tissues from most other species, including pigs. Accommodation of a transplant organ can be achieved within the organ donor with prolonged exposure of the graft to at least one accommodation inducing factor. The mechanism of antibody accommodation is not well understood. Without commitment to any one mechanistic explanation of the phenomena, it is believed that endothelial and other cells exposed in the donor to accommodation factors express agents that provide protection against antibodies in the recipient, leading to resistance.

The invention also provides for transplant tissues from a species other than donor, made resistant to preformed or developing antibodies made against the tissue in a recipient. For example, human hematopoietic cells are placed into fetal pigs under conditions that expose them to sublethal concentrations of accommodation factors. These factors are produced by cells infused into the fetal pig or could be produced by the pig or gilt/sow. The hematopoietic cells, such as granulocytes would resist destruction in a human host with antibodies against the granulocytes.

The invention also provides a method and a kit for analysis and detection of the level of accommodation within potential donor animals. The assays are performed on blood and tissues obtained from the prospective donor animal prior to transplantation of the donor organ. Analyses include detection of recipient accommodation inducing factors, for example, immunoglobulins, B cells, and T cells in the donor animal. Other analyses include in-vitro tests of resistance of circulating cells and tissues taken from the prospective donor to lysis by reactive antibodies and complement, or reactive cytotoxic T cells of the recipient. Other alternative analyses include assessment of blood and tissues from the prospective donor for over-expression of protective genes typically expressed within accommodated organs, such as heme oxygenase-1, A-20, and bcl2. Bach, F. H. et al., *Nature Medicine* 3(2): 196-204 (1997).

The invention also provides a method to asses methods and factors for accommodation and improve the accommodation method according to the invention.

A. Transplant Organs or Tissue is Accommodated Prior to Transplantation

The present invention induces accommodation of the transplant organ or tissue prior to transplantation, while the organ or tissue is still in the donor animal. Induction prior to transplantation provides major advantages. The risk of rejection of the organ graft is significantly reduced. The potential costs and complications to the patient related to efforts at preventing rejection are significantly reduced. Multiple attempts can be made at achieving accommodation in multiple donor animals, if desired, and a donor which shows indication of best transplantation results may be selected for donation of the xenograft.

A donor animal is a mammal. The mammal can be, for example, but not limited to this example, a non-human primate, an artiodactyl, a carnivore, a rodent or a lagomorph. A pig fetus is a preferred recipient of the accommodation factor.

The accommodation factor is typically an antibody or an antibody producing cell but can include other factors that induce accommodation to include, but not be limited to: antibody reactive with donor tissue, antibody reactive with donor endothelium, antibody reactive with pig tissue or endothelium in the case where the donor is a pig or a member of the swine family, plasma cells, B lymphocytes, human B lymphocytes, conditionally immortalized B lymphocytes, anti-alphaGal antibody, a cell engineered to express an accommodation inducing factor, a hybridoma comprising a cell expressing an accommodation inducing factor, T cells reactive with cells in the graft tissue or organ, perforin, and *Bandeiraea simplicifolia* lectin. The factor can be a natural, isolated factor, or it can be a cell engineered to express a ligand or the purified engineered ligand.

The accommodation factors may be derived from any mammal, for example a member of a species that would be a xenograft recipient, e.g., a human or another mammal. In a preferred embodiment, the accommodation inducing factors are isolated from an individual who will later become a recipient. The method of determining, isolating, and manipulating each of the accommodations inducing factors are well known to an artisan skilled in the art.

The process of accommodation requires prolonged exposure to the accommodation inducing factors, at least 16 hours, up to 150 days. At that point, harvesting of the organ is undertaken.

In the preferred embodiment, a pig fetus is infused at an early stage of development, preferably about 45 days. However, accommodation in an adult mammal is possible. The donor does not have to be in an immune deficient state, but must be able to allow circulating accommodation inducing factors to persist in the donor for periods of time sufficient to allow accommodation of organs and tissues. However, infusion of an immune deficient mammal is preferred.

A first step in achieving an accommodated xenograft organ is introduction of accommodation inducing factor into a donor animal. Preferably the immune components are introduced into donor at a pre-immune stage of development. For example, cells are infused into donor animals that produce sub lethal levels of ligand which bind to cells in the donor animal. The ligand induces accommodation. The cells are infused under conditions which permit stable chimerism, i.e., stable presence of recipient immune system components in the xenograft donor organism. Later, the accommodated organ for transplantation is harvested and placed into transport medium under conditions suitable for transplantation into a recipient animal.

As an example, B cells programmed to produce antibodies reactive with pig endothelium are infused into pre-immune fetal pigs. The low levels of antibodies produced bind to the endothelial cells of the pig and induce accommodation or resistance to complement dependent cytotoxicity. An organ such as a heart procured from the modified donor pig is then placed in transport medium, such as, for example, the University of Wisconsin solution and transplanted into a human recipient. In spite of the presence of antibodies reactive to pig in the human recipient, including anti-alphaGal antibodies, the organ is resistant to hyper-acute rejection.

Alternative embodiments utilize one or more sources of antibody, such as plasma cells and conditionally immortalized B lymphocytes. Cells are produced which proliferate indefinitely in vitro, but are mortalized before transplantation. For example, a thermolabile SV40 transformation gene can be inserted. The cells then proliferate at 33° C., but not at 37° C. Further safeguards can be provided by other means, such as by surrounding the transformation gene with loxP sites. The transformation gene can then be removed with Cre Recombinase. Nakamura, J., et al., *Transplantation* 63(11): 1541-1547 (1997). The cells expressing the antibodies can be from the eventual xenograft recipient, but do not need to be from to the recipient. Accommodation does not depend on the induction of tolerance in the recipient. Rather, it may depend on the prolonged expression of anti-apoptotic genes in the donor organ cells.

Additional alternative implementations would utilize T cells that are reactive with the donor animal. Perforin, the protein complex produced by cytotoxic T cells and responsible for cytolysis of target cells is structurally quite similar to the membrane attack complex. Increased resistance to cytotoxic cells is developed by exposure to perforin.

Another implementation of the invention includes the production of tissue or cells of a species different from the donor mammal. For example, human granulocytes are produced that are accommodated prior to infusion into a human patient. They would then resist rejection and destruction by preformed or developing antibodies present in the recipient. Human hematopoietic cells (preferably $10^7$/pig, range $10^1$ to $10^{10}$ per pig) would be infused into preimmune fetal pigs at 45 days gestation (range 12 days gestation to 7 days post-natal). Cells such as plasma cells, B lymphocytes, or hybridoma cells could be infused into the fetal pig that produce accommodating factors. At a later time, for example, after the birth of the pig, the human cells would be harvested and prepared in a manner appropriate for transfusion or transplantation into the recipient. The cells or the pig could be tested with assays that would predict accommodation within the human cells. For example, human cells could be tested for their resistance to cytotoxicity by antibodies or for the expression of genes known to protect cells from programmed death. The pig could be tested for the presence of antibodies reactive with the human cells.

B. Assays to Assess Donor Animals for Accommodation

The invention provides a method for assessing accommodation in the donor animal prior to transplantation of the organ. The assay allows confirmation of accommodation prior to transplantation. It also provides for a comparison of multiple donor animals infused with factors to accommodate organs, and the selection of the best candidate. The assay improves the results of transplant attempts and minimize the risk of rejection of the xenograft by preformed immune components.

To be effective, the assay needs to be predictive of accommodation and needs to preserve the organ tissue for transplantation. The ex vivo perfusion assay is considered the gold standard for predetermination of hyper-acute rejection and resistance to rejection. In accordance with the ex vivo perfusion assay, an organ, such as a heart, is perfused with serum or blood in a Langendorff apparatus. Non-accommodated organs cease functioning after a few minutes. Accommodated organs function for several hours. However, the accommodated organ is less suitable for transplantation after the procedure.

In accordance with the invention, an assay for accommodation includes a short term ex vivo perfusion of tissue other than the transplant organ. Alternatively, accommodation is gauged by testing blood cells or endothelial cells obtained from the putative donor animal for resistance to complement dependent cytotoxicity. Complement dependent cytotoxicity assays incubate the test cells with antibody known to be reactive and fresh complement. After a period of time, the viability of the cells is determined. With similar control cells, the antibody and complement kill most of the cells, while a larger proportion of accommodated cells would survive. Yet another method tests the donor animal for persistence of the infused cells, or tests the donor animal for antibodies or cells reactive with the donor animal tissue. The methods involved are well known in the art.

C. Method for Enhancement of Accommodation Within the Donor Animal

The invention provides a system for testing improvements and identification of further accommodation stimulating agents. The system consists of infusion of various factors and cells into test animals and later assessment of the modified animals for accommodation. As examples of the system, multiple sources/fractions of pig reactive antibodies are compared for their potential to induce accommodation. Each experimental group would include fetal pigs infused with the particular fraction of cells. Later the donor and/or the organs would be assessed for accommodation. Examples of tests for accommodation would include the ex vivo perfusion of an organ such as a heart or kidney and heterotopic transplantation of a xenograft into non-human primates. The cell fraction leading to the most prolonged function of the heart would be considered the most optimal. Additional objectives of the invention include the testing of different strains of donor animals and of transgenic animals.

II. Methods for Production of Accommodated Organs or Tissues in the Donor Animal The present invention provides transplant organs or tissues accommodated to be resistant to rejection by the recipient of the graft. It also provides a method for production of such accommodated organs. In accordance with the method, the organ, before harvesting, is exposed on a repeated or chronic basis to accommodating factors which bind to tissues in the donor animal but do not cause irreparable injury to the animal or the organ. Following prolonged exposure, the accommodated organ is harvested and prepared for transplantation into a recipient, such as a human.

Preferably, the ligand either needs to be infused into the donor on a repeated basis or produced by cells that are stable within the donor animal. The same or alternative or additional ligands are infused upon repeat of the infusion step. The donor animal should preferably be in a reduced immune activity state (immune deficient) in order to accept the ligand, i.e., not to immunologically reject it.

As an example of ligand infusion, human immunoglobulins are infused into pre-immune fetal pigs. The immunoglobulins are injected into individual fetal pigs by percutaneous injection using ultrasound guidance. Sub-lethal levels of the accommodating factors are infused.

The levels of factor to be infused is pre-determined in empirical fashion. For example, a serum fraction is used and increasing concentrations are administered to at least one other fetus, at similar stages of development. An $LCD_{50}$ is determined and preferably used as an accommodation treatment. Any $LCD_n$, where n≦90% of the lethal dose is useful as an accommodation factor dose.

The immunoglobulins include antibodies, including IgG and IgM, which specifically binds pig endothelial cells. Examples of such antibodies include anti-alphaGal present in humans and Old World primates. Galili, U., et al., *Blood*, 82(8): 2485-2493 (1993). AlphaGal is not expressed in these animals, but is expressed in most other species, including pigs. The immunoglobulins may include antibodies to other xenogeneic antigens as well.

The method of preparation of such antibodies or isolation of enriched fractions of such antibodies are well known to artisans skilled in the art. For example, serum can be passed through an immunoadsorption column containing alphaGal. After washing the column, the adherent anti-alphaGal antibodies is eluted. Active antibody fragments or active single donor antibodies can also be employed.

Another example of a ligand would be the lectin *Bandeiraea simplicifolia* which binds to alphaGal, including the alphaGal expressed on pig endothelial cells. Grehan, J. F., et al., *Transplant. Proc.* 32(5):975 (2000). The lectin is infused at low levels (less than 100 μg/ml) into putative donor pigs. It is infused on a daily basis for 3 to 30 days.

B lymphocytes committed to production of antibodies or plasma cells producing antibodies reactive with the donor tissue are infused under conditions allowing stable engraftment and providing sub lethal doses of antibodies. As an example, human B lymphocytes ($2 \times 10^8$/kg, range $1 \times 10^6$/kg to $4 \times 10^9$/kg) would be infused by ultrasound guidance into fetal pigs at 45 days gestation (range 30 to 80 days) under sterile conditions. It is estimated that approximately 1% of the human B cells would be committed to production of antibody to alphaGal. Because the B cells are infused into pre-immune fetal pigs, the fetal pigs would accept the B cells and become tolerant to such cells.

The accommodation inducing factors, be they a ligand or a suspension containing immune cells, can be from an individual unrelated to the recipient. Accordingly, the cells may include B cells from unrelated humans or from other species. For example, human B cells from a type O individual can be infused into fetal baboons of type A or B. The low levels of anti-A or anti-B induce accommodation. The transplant organ could then be harvested for transplantation after the birth of the baboon. The infused cells may include immortalized cells such as hybridoma cells. In accordance with one embodiment, an accommodation-inducing cell, preferably a B lymphocyte would contain a suicide gene such as thymidine kinase or adenosine deaminase. Cohen, J. L., et al., *Hum. Gene Ther.* 11(18): 2473-2481 (2000). Prior to transplant, the cells could then be purged with the appropriate prodrug.

In a preferred embodiment, the accommodation inducing factors are from the same species as the recipient. In accordance to another preferred embodiment, the accommodation inducing factor is from the individual who will be the ultimate recipient. Because accommodation is a property of the transplant organ, it is not essential to adoptively transfer lymphocytes back to the recipient.

Following prolonged exposure (preferably more than 20 days, range 16 hours to 150 days), the donor animal is euthanized under conditions that permit procurement of the donor organ suitable for transplantation. For example, if the organ for transplant is a pig heart, the donor pig with accommodated tissues is sedated and anesthetized with isoflurane. Under sterile conditions, the chest is opened and cold Cardioplegia solution (such as Stanford solution containing mannitol, potassium chloride, sodium bicarbonate) is infused into the pig aorta and the heart is packed in iced saline. The heart is removed and perfused with transport medium, such as Eurocollins solution (Steffen, R., et al., *Transpl. Int.* 3(3):133-136 (1990)) or University of Wisconsin solution (Belzer, F. O. and Southard, J. H. *Transplantation* 45(4): 673-676 (1988)) The organ preservation solutions contain essential amino acids, carbohydrates, and electrolytes that maintain viability of the organ or tissue during transportation to the recipient.

Organs that may be accommodated are, for example, but not limited to for transplantation prior to transplantation include, but are not limited to heart, kidney, liver, lung, pancreas, heart-lung, intestine, spleen, or thymus. Tissues that may be accommodated include, but are not limited to bone, skin, hair, retired pigmented cells, neural tissue, skeletal muscle, myocytes, pancreatic islets, hepatocytes, embryonal or adult stem cells, and hematopoietic cells.

Another implementation of the invention relates to the production of accommodated tissue or cells of a species different from the donor mammal. Such tissue or cells may include, but are not be limited to, osteo blast cells, osteo clost, skin, skin epithelial cells, hair follicle cells, eye, neural cells, skeletal muscle, smooth muscle cells, cardiac muscle cells, pancreatic islets, hepatocytes, stem cells, progenitor cells, or hemapoietic cells. Such cells would be derived from an animal of a species other than the donor. Preferably, they would be from the same species as an eventual recipient, or even from the recipient himself. The donor animal could be any of the donors of the invention.

Accommodation factors in accordance with the invention could be administered prior to administration of the cells for accommodation (one hour to two days), at the same time as the cells for accommodation or shortly after the cells for accommodation are administered. In a preferred embodiment, the cells for accommodation and the accommodation inducing factors are administered at the same time, mixed together, or within minutes of each other. The accommodation inducing factors are factors in accordance with the invention, but may further include an antibody, an antibody producing cell, or a T-cell which recognizes cells from the species where the cells to be accommodated are derived.

After prolonged exposure in accordance to the invention, the state of accommodation of the cells of a species different from the donor mammal could be assessed by any of the methods of the invention, for example by looking for antibodies in the donor specific for the cells introduced for accommodation. Finally, the accommodated cells or tissue are harvested.

The cells introduced for accommodation or their progeny can be separated by positive means or by negative means from donor cells. For example, the donor can be from a species engineered with a conditionally lethal gene, for example the *thymidine kinase* (HSV-tk) gene. Cells harboring this gene are sensitive to ganciclovir. Moolten and Wells *Cancer Res.* 46: 5276-5281 (1986); Reardon *J. Biol. Chem.* 264:19039-44 (1989); and Patil et al., *Breast Can. Res. Treat.* 62: 109-115. Upon harvesting, donor cells can be killed, by exposure to ganciclovir. Alternatively, the cells to be accommodated are transformed with a positive selection, prior the being administered into the donor. They can be engineered to express a selective marker, such as drug resistance, or an antigen that will upon expression be located on the cell membrane such that an antibody specific to the antigen may fish out a cell expressing the antigen. Those and similar approaches are well known to an artisan skilled in the art.

For example, human granulocytes could be produced that are accommodated prior to infusion into a human patient. They would then resist rejection and destruction by preformed or developing antibodies present in the recipient. Human hematopoietic cells (preferred $10^7$/pig, range $10^1$ to $10^{10}$ per pig) would be infused into preimmune fetal pigs at 45 days gestation (range 12 days gestation to 7 days post-natal). Accommodation inducing factors such as plasma cells, B lymphocytes, or hybridoma cells could be infused into the fetal pig that produce accommodating factors. At a later time, for example, after the birth of the pig, the human cells would be harvested and prepared in a manner appropriate for transfusion or transplantation into the recipient. The cells or the pig could be tested with assays that would predict accommodation within the human cells. For example, human cells could be tested for their resistance to cytotoxicity by antibodies or for the expression of genes known to protect cells from programmed death. The pig could be tested for the presence of antibodies reactive with the human cells.

While pigs would be an ideal species donor mammal for accommodation, the invention can be readily implemented with any of many animals. Animals that can potentially be used as surrogates i.e. donors, include, but are not limited to those listed below. It is known that some animals offer advantages for select uses.

Preferred donors are mammals. From among 39 major orders of the class Mammalia, five orders appear particularly suitable as surrogate animals for human organ recipients: primates, artiodactyls, carnivores, rodents, and lagomorphs.

The primates, other than human, are suitable from the standpoint of organ function. Amino acid sequencing of proteins typically demonstrate 90 to 98% homology with humans. Organs such as livers and hearts function well when transplanted into humans. The primates are concordant with humans, i.e. human recipients do not typically have performed antibodies to the tissues of the primates.

While some of the lower primates, such as lemurs, have short gestation periods (132-134 days), the higher primates (chimpanzees, gorillas) have gestation periods approximating that of humans (267 days).

The artiodactyls, even-toed ungulates, include several domesticated animals such as swine, sheep, goats, and cows. Organs or proteins from several members have been demonstrated to be functional and useful in humans or have been proposed for transplantation. For example, porcine and bovine insulin, pig skin, sheep hearts, etc. have been used or proposed for therapeutic use.

The gestation periods vary between the members of this order. Pigs have a period of 114 days. Sheep have a period of 145 days. Cows have a gestation period of 282 days. Cows offer features that are potentially useful for surrogate tolerogenesis. The placental blood of all of the littermates is shared. Therefore human cells infused into a single calf should lead to tolerance to all of the littermates.

The carnivores, including dogs, cats, etc., have several features that are potentially advantageous for surrogate tolerogenesis. Many have short gestation periods (cats about 65 days, dogs about 63 days) and the newborn are relatively well developed. The canine and feline immune systems are very similar to the human immune system. The feline immunodeficiency virus model in cats is one of the few animal models available for the study of AIDS.

Cats and dogs have been commonly used as large animal models for transplantation, including bone marrow, lung, intestine, and bone transplants. Ladiges et al., *Lab. Anim. Set,* 40: 11-15 (1990); and Henry, et al., *Am. J. Vet. Res.,* 46: 1714-20 (1985).

The rodents, including rats, mice etc. are potentially useful for surrogate tolerogenesis because of their short gestation periods and rapid growth to maturity. For example, rats have a gestation period of only 21 days and grow to maturity in only 6 weeks. Because the immune system of rodents is very immature at birth, tolerance can be induced by injecting cells within 24 hours of birth rather than by intrauterine injections.

The lagomorphs, which includes rabbits and hares, were once considered part of the rodent order but have been recently separated. They share with the rodents a very short gestation period and short maturation periods. Thus, they would also be useful for the development of new donor strains, including transgenic strains favorable providing functional organs or tissues. Their larger size would make these animals better surrogate candidates than rodents.

The ideal surrogate species should preferably be phylogenetically close to the intended organ graft recipient. Also, the physiology of the intended graft should be similar to the physiology of the organ graft recipient organ or tissue to be replaced by the graft.

Additional considerations influence the choice of species for surrogate tolerogenesis. The transplanted graft is to be approximately the same size as the corresponding graft within the organ graft recipient.

Consequently, with the additional considerations described above, pigs are preferable surrogates over primates, because pigs have a gestation period of only 114 days and typically grow to over 59 kg by four months of age.

Pre-immune fetal animals provide an ideal environment for infusion of B cells or plasma cells. The earliest fetus that could be infused with an accommodation inducing agent would be the first stage with a circulatory system and beating heart. The fetal development proceeds at different rates in different species. However, this stage is known in the art as the Carnegie stage 10 (4 to 12 somites). Human fetuses at this stage are 2 to 3.5 mm in length. William J. Larsen, ESSENTIALS OF HUMAN EMBRYOLOGY, Churchill Livingstone, p. xi (1998).

When the donor is a fetus, maternal factors may contribute to accommodation. Many factors are transported from maternal circulatory system to the fetal circulatory system. For example, all four subclasses of IgG are transferred across the placental membrane. Coulam et al., eds., IMMUNOLOGICAL OBSTETRICS p 295, WW Norton & Co. (1992). Placental transfer begins at the midpoint of the first semester (about 17 days in pigs) and continues at a low level through the se4cond trimester (approximately 76 days in pig). In vitro, low levels of IgG were shown to accommodate porcine endothelial cells. Dorling et al., (1998), supra. Therefore, circulating IgG or other factors in the mother, either introduced by infusion, or produced by the mother, would be transferred across the placenta to the fetus, leading to accommodation in the fetus.

There are alternative ways in which an accommodation-inducing factor, for example, B cells or plasma cells, may achieve stable engraftment and produce anti-donor antibodies. For example, B cells may be infused into animals that are immune deficient due to chemotherapy or irradiation or are immune deficient due to congenital defect such as severe combined immune deficiency. The mammal may receive bone marrow or stem cell transplants, similar to the method used for human bone marrow transplants. Armitage, J. O., *Blood* 73(7): 1749-1758 (1989). Mammals with a congenital immune deficiency such as severe combined immune deficiency can be infused with foreign cells, such as human hematopoietic cells. McCune, J. M., et al., *Immunol. Rev.* 124: 45-62 (1991).

Stable engraftment could also be achieved by infusing cells into the donor animal that are not antigenically recognized by the donor animal. As an example, porcine B cells could be transfected with a gene producing an antibody reactive with porcine endothelial cells. These cells could then be infused into pigs to be used as donor animals.

Under specific circumstances, the factors may be administered by any route known to a skilled artisan, as, for example, oral, intravenous, intramuscular, intra-arterial, intramedullary, intrathecal, intraventricular, transdermal, subcuterion, intraperitoneal, sublingual, or rectal. The preferred manner of administration of the accommodation inducing factors is by infusion.

The factors are delivered in pharmaceutically accepted formulations. They can be aqueous, preferably in a physiologically compatible buffer, e.g. Hank's solution, Ringer's solution or buffered saline. Alternatively, powders, gels, emulsions may be administered. The formulations depend on avenue of delivery and are well known to an artisan skilled in the art. For a discussion of formulations and administration methods, see REMINGTON'S PHARMACEUTICAL SCIENCES (Maack Publishing Co., Easton, Pa.)

III. Methods for Assessment of Transplant Organ Accommodation Prior to Transplantation After the above procedures have been performed, the optimal utility would be achieved by analyzing the donor pigs or tissues from donor pig to determine if accommodation has been achieved and to quantify the accommodation. In general the test should be relatively rapid and cost-effective. It should be predictive of the graft survival. It should not interfere with the organ to be transplanted.

Analysis of the donor animal for predictive evidence of accommodation would achieve three basic goals. First, the analyses provides quality assurance and confirmation of accommodation. If accommodation is not achieved in the tested donor animal, the transplant could be postponed or another animal could be used. Second, tests of accommodation can confirm if the graft is specifically accommodated for a particular patient. Third, the analyses permit the comparison of multiple potential donor animals and the selection of the most suitable animal for transplantation.

The analyses of accommodation can be accomplished via any of four basic approaches: in vitro assays of rejection, detection of genes in tissue that convey protection against rejection, detection of either cells or immunoglobulins infused in the donor animal prior to organ harvesting and detection of antibodies in the test animal reactive with the donor animal.

In the first approach, tissue from the donor animal is assessed in vitro. Plasma or serum from the recipient, or a sensitized animal similar to the recipient, is infused through tissue from the test animal. If accommodation was not achieved, the tissue would cease functioning shortly after perfusion. If accommodation is achieved, however, the tissue continues to function. As an example, in the Langendorff assay, heart grafts that are perfused with plasma, serum, or blood containing cytotoxic antibodies stop beating in about 20 minutes. If accommodation is achieved, however, the graft would beat for two to four hours. Therefore the heart graft obtained for transplantation could be perfused with sensitized plasma. If it were still beating strongly at the end of 45-60 minutes, accommodation would be demonstrated. The heart graft could then be stopped with cardioplegia and perfused with transport medium until transplanted. See Examples 2 and 4.

In an alternate and preferable embodiment, another organ from the donor animal is tested. For example, if the transplant organ were a kidney, the heart or the contralateral kidney could be tested for function with the Langendorff assay. Accommodation would be considered to be achieved if the test organ continues to be considered viable for at least a 50% longer time interval, preferably at least a 100% time interval, than the typical time an equivalent organ which did undergo an accommodation-inducing step is deemed viable.

In another implementation of the in vitro test of rejection, peripheral blood leukocytes or endothelial cells from the chimeric donor mammal is incubated with serum containing antibodies which specifically bind to donor mammal tissue and complement. Complement mediated lysis of cells from the donor is determined. If accommodation is achieved, lysis is significantly reduced compared to lysis of a similar unmodified animal. See also Example 3.

Viability can also be determined with other dyes. For example, dead cells will accumulate propidium iodide and can be detected by flow cytometry. Cells can be labeled with radioactive Chromium-51. When killed, the radioactivity is released. After removing the cells and membranes, the free radioactivity is measured. Shimizu, Y., et al., *J. Immunol. Methods* 164: 69-77 (1993). See Example 5.

The second basic approach of analyses for accommodation would test tissue from the modified animal for expression of genes that protect tissues from hyper-acute rejection. These gene products make cells resistant to cellular death by apoptosis and prevent expression of proinflammatory genes including cytokines, procoagulant and adhesion molecules. Examples of these genes include heme oxygenase, A-20, and Bcl-2. They have been observed in grafts that become accommodated following prolonged transplantation in a sensitized recipient.

In accordance to the present invention, in one embodiment, a biopsy is taken from the test donor animal, such as a pig modified as described above to induce accommodation to preformed anti-pig antibodies. The biopsy could be from the transplant organ, such as needle biopsy of the left ventricle of the heart. Alternately, it could be from another organ or tissue. If the transplant organ were to be the heart, it could be a biopsy from the kidney, skin, or a sample of blood. The tissue is examined for the presence of the above genes using standard antibody-based assays such as immunohistochemistry, Western blots, and ELISA assays, and RNA using Northern blots and polymerase chain reaction assays. The results are compared with positive and negative controls. Monoclonal antibodies for Bcl-2 can be obtained from Transduction Laboratories (Lexington, Ky.) and for heme oxygenase from StressGen (Victoria, BC, Canada). Monoclonal antibodies against A-20 were prepared by Dr. V. Dixit (Ann Arbor, Mich.). A probe can be devised or primers can be devised and purchased or synthesized on a DNA synthesizer by methods well known in the art. Because others have not accommodated an organ while still in the donor, there was no reason to have tested the donor organ for enhanced expression of the gene prior to transplantation. Neither was there any reason to test tissues from the donor animal other than the transplant organ for evidence of accommodation.

The third approach to detection and quantification of accommodation assesses evidence of chimerism within a donor animal with infused cells or which was treated with an accommodation-inducing factor immunoglobulin. These parameters can be readily assayed and provide indirect evidence of accommodation. If the donor animal rejected the infused cells and the immunoglobulins were undetectable, it is unlikely that accommodation of an organ or tissue was achieved. Similarly, their persistence is predictive of accommodation.

A sample of anticoagulated blood or serum is obtained from the modified donor animal, such as a pig infused as a fetus with B cells. The peripheral blood lymphocytes are stained for chimeric lymphocytes and the number of cells quantified with analytical flow cytometry. As an example, if the pigs were infused with human B cells, the lymphocytes from the modified pig could be stained for human B lymphocytes with an antibody specific to CD20. The CD20 is specific of the species providing the accommodation factor. The amount of chimerism would be compared with appropriate positive and negative controls. The lymphocytes are alternately assayed for DNA present only in the infused cells. The DNA is detected by polymerase chain reaction or restricted length fragment polymorphisms.

In accordance with an alternative embodiment, the cells infused into the donor animal are labeled with a marker that is readily detected. For example, the infused cells may contain a transgene containing green fluorescent protein (GFP). Blood from the modified donor animal is examined directly for GFP by fluorescence microscopy or by flow cytometry.

In another embodiment, the serum is assayed for immunoglobulins produced by the infused cells. Human immunoglobulins, for example, could be quantified using standard assays such as an ELISA assay. See Example 6.

The fourth approach to analyses of the modified donor animal for accommodation is by detection of antibodies specific to the donor tissue or to cells producing antibody which specifically binds the donor tissue. Serum or anticoagulated blood is obtained from the donor animal pretreated with an accommodation-inducing factor, such as a pig infused with human B cells reactive with pig endothelial cells. The serum is co cultured with porcine endothelial cells. The cells are washed and labeled with peroxidase-conjugated anti-human IgG and IgM, followed with the appropriate substrate. The presence of low levels of anti-pig antibody is a positive result. The values are compared with appropriate negative and positive controls. Alternatively, lymphocytes obtained from the modified donor animal are maintained in culture. The spent supernatant is assayed for production of anti-donor antibodies. Alternatively, immunoglobulins are isolated from one or more of tissues from the modified donor animal. For example, if the transplant organ is a heart, a kidney is removed from the modified animal and perfused with an acidic buffer (pH2 to pH4) such as glycine buffer. The antibodies collected in the eluate are assayed for anti-donor antibodies.

IV. Methods for Improvement of Accommodation Procedures

The present invention provides an experimental system for testing improvements to the donor organ accommodation and, in particular, the testing of accommodation factors. In particular, the invention allows for quantification of accommodation.

As an example of implementation of the system, multiple sources of anti-pig antibody are assayed to develop optimal accommodation of pig xenografts. Potential sources of antibodies include B cells isolated from an unsensitized human, B cells isolated from a sensitized human, B cells isolated from sheep, a B cell line known to produce antibodies to alphaGal, liposomes containing *Bandeiraea simplicifolia*, etc. Litters of pre-immune fetal pigs are infused with increasing doses of the antibody or cells expressing antibody using ultrasound guidance, until the toxicity causes abortion of the fetal pigs. Using a sub lethal dose of the test source, such as 50% of the lethal dose, fetal pigs are infused with the test source. After birth of the pigs or Caesarian section of the sows, the test pigs are assayed for accommodation using any of the above described tests. At various ages, heart grafts are harvested from appropriate pigs and tested by the Langendorff assay, perfusing the graft with sensitized plasma or blood, such as human blood. The optimal antibody or antibody producing cell is the one that provides the most prolonged function in the Langendorff assay and provides for persistence of accommodation after birth. A minor population of the tested accommodation inducing material is further tested with xenotransplantation into sensitized recipients, such as baboons.

The system can also be used to test sources of animals for accommodation, including different strains of pigs, transgenic pigs, or other mammals.

The present invention, thus generally described, will be understood more readily by reference to the following examples, which are provided by way of illustration and are not intended to be limiting of the present invention.

EXAMPLES

Example 1

Prevention of HAR in Sensitized Sheep Using Chimeric Pigs

Methods. Chimerism in three donor pigs was induced by infusing a suspension of lymphocytes obtained from a sheep (either the recipient sheep or an unrelated sheep) into pre-immune fetal pigs at 45 days gestation. The suspension includes B cells programmed to produce antibodies reactive with pig cells. Later the pig heart was procured from the donor and a heterotopic pig heart transplant was performed.

Results. The results are presented in Table 1. The chimeric grafts were rejected at 3+, 9+ and 25 days in sensitized recipients compared with vascular rejection at 0.5-2 days for the non-chimeric controls.

The prolonged survival of the grafts was not due to tolerance. Indeed, the second sensitized sheep demonstrated a titer of cytotoxic antibodies to pig at greater than 1 to 2000 by seven days post-transplant, yet continued to function appropriately.

The third experimental transplant was a sheep unrelated to the sheep used for chimerism. It was intentionally sensitized with pig lymphocytes three times prior to the transplant.

Conclusions. Chimerism appears to provide protection against hyper-acute rejection in sensitized sheep. The third recipient suggests that the accommodation is not a function of an individual sheep. It is highly unlikely that the observed prolongation of graft survival was due to induction of tolerance. Indeed, one of the recipients demonstrated a typical second set sensitization. Second set sensitization refers to the immune reaction following a repeated exposure to the antigen. It is typically more rapid, higher tittered, and involves memory cells and IgG.

TABLE 1

Heart Xenograft Survival In Sensitized Recipients

| Experimental Group | Donor Pig Chimerism | Pre-tx Anti-Pig Antibodies | Xenograft Survival (Days) | Xenograft Pathology |
|---|---|---|---|---|
| Control* | No | 64 | 0.5 | Severe vascular rejection |
| Control* | No | 4 | 1 | Severe vascular rejection |
| Control | No | 4 | 2 | Severe vascular rejection |
| Chimeric Experimental | Yes | 16 | 9+ | No rejection |
| Chimeric Experimental | Yes | 4 | 25 | Mild cellular rejection, ischemic infarct |
| Chimeric Unrelated Experimental* | Yes | 16 | 3+ | Mild rejection, hematoma |

*Sheep sensitized with pig lymphocytes three or more times.
+Sheep euthanized for technical reasons. Graft rejection was absent to mild.
The pre-tx stands for prexenograft transplantation.

Example 2

Function of Chimeric Sheep to Pig Heart in Langendorff with Sensitized Sheep Plasma In this study, chimeric pig hearts were assessed for function in the Langendorff apparatus and compared with non-chimeric hearts. Previous studies showed this assay to be predictive of in vivo function.

Sheep bone marrow was prepared and infused into fetal pigs at 45 days gestation. At term, the pigs were delivered by Cesarean section. Blood was analyzed for chimerism by polymerase chain reaction employing primers specific for class I histocompatibility antigen, and flow cytometry. Heart grafts were isolated from chimeric or non-chimeric pigs and suspended in a Langendorff apparatus. The coronary arteries of the graft were perfused with Krebs-Heinsleit solution. After beating for 30 minutes, plasma from unsensitized sheep or sheep sensitized 3 to 5 times with pig lymphocytes was added. Neither the sheep nor the pig lymphocytes used for sensitization were related to the sheep or pig in the chimeric hearts. Complement dependent lymphocytotoxicity assay demonstrated that the sensitized sheep plasma had titers of 32 to 128. The graft was analyzed for heart rate, perfusion pressure, and coronary flow rate until the graft stopped beating (<30 beats/minute).

Results: Normal control hearts perfused with plasma from unsensitized sheep functioned as long as four hours. Normal control hearts perfused with plasma from highly sensitized sheep stopped beating at 19+/−12 minutes (7 to 40 minutes, n=6). These included 2 pigs with minimal chimerism (<1%) and 1 pig from an injected sow with no detectable chimerism. Hearts from chimeric pigs (3 to 11% by flow cytometry) beat for 183+/−46 minutes (137 to 229 minutes, n=3). The difference was significant, P<0.0001. Immunofluoesence stains demonstrated less IgG and IgM deposition in the vessels of the chimeric hearts.

Conclusions: In the presence of high titers of cytotoxic anti-pig antibody, normal pig hearts stopped beating in less than 20 minutes while the chimeric hearts continued beating for 3 hours. Resistance to rejection depended on factors within the heart graft rather than circulating factors or cells. The protective effect was not specific for a particular sheep or particular pig. The sheep used for plasma for the perfusion was sensitized with pig lymphocytes not related to the pig source of the heart. That sheep was also unrelated to the sheep whose cells were infused into the fetal pig.

One pig with minimal chimerism and 2 pigs from injected sows but no detectable chimerism showed no evidence of accommodation and the heart grafts stopped beating shortly after adding the plasma from a sensitized sheep. These observations demonstrate the value of analyses of pigs prior to organ procurement.

Example 3

Accommodation of Leukocytes in Chimeric Pigs

Methods: Peripheral blood lymphocytes were obtained from normal pigs and from chimeric pigs injected with sheep marrow at the pre-immune fetal stage. The lymphocytes were incubated with tittered serum from a sensitized sheep and with human serum containing cytotoxic antibodies to alphaGal. Fresh rabbit complement was added. Cytotoxicity was determined with Trypan blue. The titer was determined at the greatest dilution with 20% or more cytotoxicity.

Results: The peripheral blood of three test pigs showed chimerism with sheep cells, varying from 2.7% (72-3) to 4.6% (72-5).

Peripheral blood lymphocytes from the three chimeric pigs have at least partial resistance to lysis by a sensitized serum. At a dilution of serum causing 100% lysis of control pig lymphocytes, it caused lysis of only 11%, 31%, and 47% of the lymphocytes from the chimeric pigs. See FIG. 1.

The accommodation of pig 72-5 was confirmed by lysis of lymphocytes with serum from a second sensitized sheep. At a dilution causing 90% lysis of normal pig lymphocytes, the serum caused only about 15% lysis of the lymphocytes from the chimeric pig. See FIG. 2.

Conclusions: The peripheral blood lymphocytes from the chimeric pigs demonstrated resistance to complement mediated cytotoxicity. This protection cannot be accounted for by the presence of sheep lymphocytes, since the chimerism was less than 5%. The heart from piglet 72-5, demonstrating the greatest accommodation of lymphocytes, was tested for accommodation in an ex vivo perfusion study using human blood.

Example 4

Prolonged Function of a Pig Heart Accommodated by Sheep Factors when Perfused with Human Blood Methods: Pre-immune fetal pigs were infused with sheep marrow as described in Example 3. After birth, the blood is analyzed by PCR and flow cytometry for chimerism with sheep cells. Accommodation was assessed by measuring the resistance to complement dependent antibody cytotoxicity, as illustrated in Example 3. The heart explants from the best chimeric pig (72-5) and a control pig were perfused ex vivo with blood from a human volunteer (type B) using the Langendorff apparatus. J. J. Dunning, et al., *Eur. J. Cardiothorac Surg.* 8:204-206, (1994). The duration of heart function was determined. Sections of the heart explants were fixed in formalin and evaluated with routine hematoxylin and eosin sections.

Results: Consistent with the studies by Dumming, Id., the control pig heart became bradycardic within 20 minutes of perfusing it with whole human blood. The ventricles stopped at that time. When human blood from the same volunteer was perfused through a heart graft from a chimeric pig (injected with sheep marrow), it initially demonstrated some slowing (from 132/minute to 70/minute). By 20 minutes, however, the rate recovered to 80% of the initial rate. By 80 minutes, the rate recovered to 100% of the initial rate. The heart continued to beat strongly for 4 hours, when the assay was terminated. See FIG. 3.

The histology of the control graft showed evidence of hyperacute rejection, including thrombi of platelets and fibrin, margination of neutrophils, and interstitial hemorrhage. The myofibrils had evidence of ischemia, with hypereosinophilic cytoplasm, pyknotic nuclei, and vacuolization. In contrast, sections of the experimental heart did not show thrombi, neutrophil margination, or ischemia. Immunofluorescence stains were done for human IgG, IgM, C3, and C9. The heart from the chimeric pig had less deposition of IgM, C3, and C9 than the control heart. There was no appreciable difference in IgG deposition.

Conclusions: The study demonstrates prolonged function of a sheep factor chimeric heart when exposed to human blood. Because sheep constitutively produce alphaGal, they do not develop natural antibodies to alphaGal, in contrast with humans. Therefore, the protection of the graft by accommodation to anti-alphaGal was produced by antibodies to pig associated antigens other than alphaGal.

Example 5

Persistence of Accommodation in Chimeric Pigs

Introduction: In this study, accommodation was assessed in 12 and 15-week-old swine.

Methods: Peripheral blood lymphocytes were isolated from accommodated and control swine. The lymphocytes were incubated with serum from a sensitized sheep (titer 1:128) and fresh rabbit complement. The sensitized serum was used at a dilution of 1:4. The killed lymphocytes were quantified with propidium iodide and flow cytometry. The sensitized serum and complement killed 96 to 100% of pig lymphocytes from eight control pigs with these conditions. The viability of the control lymphocytes, therefore, was equal to or less than 4%. By contrast, 73% or more of lymphocytes from accommodated swine were viable. See Table 2.

TABLE 2

| Pig | Viability at 2 wks* | Current Viability* | Current Swine age | Current Swine weight (kg) |
|---|---|---|---|---|
| 421-3 | 83% | 79% | 12 weeks | 77 |
| 421-10 | 80% | 84% | 12 weeks | 74 |
| 2160-2 | 90% | 83% | 12 weeks | 78 |
| 2163-1 | 87% | 90% | 12 weeks | 80 |
| 2141-2 | 79% | 73% | 15 weeks | 94 |

*Control lymphocytes (n = 8) had viability equal to or less than 4%.

Discussion: The accommodation of the lymphocytes observed in two-week-old pigs persisted until tested at 12 or 15 weeks of age. At this age and weight, the swine would be appropriate donors for adult human recipients. Assuming that endothelial cells have a similar level of protection, the accommodated organs would provide protection against hyperacute rejection and acute vascular rejection.

Example 6

Presence of Sheep IgG in Accommodated Chimeric Pigs and Transplantation Results Introduction: Accommodation is believed to result from the induction of protective proteins in cells with bound immunoglobulin. A possible mechanism of accommodation in the chimeric pigs, therefore, would be the production of sublethal levels of antibodies by the infused xenogeneic cells. In this study, serum samples from donor pigs were analyzed by ELISA for sheep IgG.

Methods: A sandwich ELISA assay was developed for sheep IgG. The microtiter plates were coated with donkey anti-sheep IgG, blocked with Tween 20 and washed. The test serum was added at multiple dilutions and incubated for 30 minutes. After washing, biotinylated donkey anti-sheep IgG was added to the plates. After washing, the plates were developed with streptavidin peroxidase, followed by substrate. The reaction was stopped with sulfuric acid and the plates were read with a microplate reader. The assay was performed with serum from four control sheep, 14 control pigs, and 12 pigs (10 to 14 days) from sows carrying pigs injected with sheep marrow cells. Hearts were harvested and transplanted into recipient sheep. Post-transplant, the sheep received cyclosporine (300-800 ng/ml trough level) and tapered steroids. The hearts were biopsied weekly. See Table 3.

Discussion: The presence of chimeric IgG in the chimeric pigs was detected using a specific ELISA assay. The findings are significant for three reasons. First, the presence of IgG is consistent suggests that low levels of antibodies bind to pig cells and induce accommodation. Second, the assay provides the means to monitor efforts at improving accommodation by enhancing B cell chimerism and function. Third, the assay is useful for quality assurance, assessing potential donor pigs prior to procuring the organ for transplantation.

This study does not define the specificity of chimeric IgG in predicting graft outcome. However, none of the heart xenografts from pigs with detectable IgG developed apparent rejection during the course of the study. Two sheep, however, were euthanized at 5 and 17 days due to technical failures. Two sheep were euthanized at 30 days according to the protocol. One graft was free of rejection after 106 days.

TABLE 3

| Pig | Sheep IgG (ug/ml) | Recipient Sheep | Graft Survival | Outcome |
| --- | --- | --- | --- | --- |
| 2141-4 | 0.64 | 105 | 5 days | No rejection, technical failure |
| 395-4 | 1.00 | 106 | 106 days | No rejection |
| 1187-5 | 1.08 | 116 | 17 days | No rejection, technical failure |
| 2165-5* | 2.16 | 110 | 30 days | No rejection, euthanized |
| 2161-2* | 4.64 | 97 | 30 days | No rejection, euthanized |
| 1115-7# | Not detected | 101 | 6 days | Acute vascular rejection |
| 2141-8# | Not detected | 112 | 7 days | Acute vascular rejection |
| 1115-5 | Not detected | 113 | 5 days | No rejection, technical failure |
| 2126-5 | Not detected | 103 | 9 days | Acute cellular rejection |
| 2165-3 | Not detected | 115 | 15 days | Acute cellular rejection |
| 385-1 | Not detected | 102 | 24 days | Acute cellular rejection |

TABLE 3-continued

| Pig | Sheep IgG (ug/ml) | Recipient Sheep | Graft Survival | Outcome |
| --- | --- | --- | --- | --- |
| 1163-3 | Not detected | 107 | 25 days | Acute cellular rejection |
| Control pigs (n = 14) | Not detected | | | |

*Lymphocytes from pigs 2165-5 and 2161-2 were also tested with the lymphocytotoxicity assay for accommodation. See Example 5. Using conditions in which the viability of control lymphocytes was equal to or less than 4%, the viability of 2165-5 lymphocytes was 98%. The viability of 2161-2 lymphocytes was 95%.
Control transplants. Pigs did not have detectable chimerism by PCR or flow cytometry.

The invention claimed is:

1. A method for providing a tissue or organ resistant to complement-dependent cytotoxicity mediated by preformed antibodies reactive with donor antigen in a sensitized recipient mammal, comprising the steps of:
   (i) infusing a first donor mammal at least one time with sub-lethal levels of bone marrow from a sensitized recipient mammal,
   (ii) administering a tissue or organ from a second donor mammal to the first donor mammal;
   (iii) allowing prolonged exposure of the first donor mammal to the bone marrow,
   (iv) harvesting the tissue or organ of the second donor mammal from the first donor mammal; and
   (v) determining that the tissue or organ of the second donor mammal is resistant to complement-dependent cytotoxicity mediated by preformed antibodies of the sensitized recipient mammal reactive with donor antigen,
wherein the method does not include administering an accommodation-inducing factor other than bone marrow; and wherein the first donor mammal is a non-human pre-immune fetal donor mammal.

2. The method of claim 1, wherein the sensitized recipient mammal is a human.

3. The method of claim 1 wherein step (ii) is performed after step (i).

4. The method of claim 1 wherein the method provides the organ and the organ is selected from the group consisting of heart, kidney, lung, liver, pancreas, intestine, spleen, and thymus.

5. The method of claim 1, wherein the method provides the tissue and the tissue is selected from the group consisting of bone, skin, neural tissue, skeletal muscle myocytes, smooth muscle myocytes, cardiac muscle myocytes, pancreatic islets, hepatocytes, stem cells, progenitor cells, and hematopoietic cells.

* * * * *